(12) United States Patent
Myers et al.

(10) Patent No.: US 10,888,273 B2
(45) Date of Patent: Jan. 12, 2021

(54) PERSONAL HYDRATION MONITOR

(71) Applicant: North Carolina State University, Raleigh, NC (US)

(72) Inventors: Amanda Myers, Raleigh, NC (US); Abhishek Malhotra, Raleigh, NC (US); John Muth, Raleigh, NC (US); Yong Zhu, Raleigh, NC (US); Shanshan Yao, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 932 days.

(21) Appl. No.: 15/160,594

(22) Filed: May 20, 2016

(65) Prior Publication Data

US 2016/0338639 A1 Nov. 24, 2016

Related U.S. Application Data

(60) Provisional application No. 62/164,154, filed on May 20, 2015.

(51) Int. Cl.
*A61B 5/00* (2006.01)
*A61B 5/053* (2006.01)

(52) U.S. Cl.
CPC .......... *A61B 5/4875* (2013.01); *A61B 5/0531* (2013.01); *A61B 5/681* (2013.01); *A61B 5/6824* (2013.01); *A61B 5/002* (2013.01); *A61B 5/6828* (2013.01); *A61B 5/6829* (2013.01); *A61B 2503/10* (2013.01); *A61B 2503/40* (2013.01); *A61B 2560/0214* (2013.01)

(58) Field of Classification Search
CPC ... A61B 5/14521; A61B 5/681; A61B 5/4875; A61B 5/0531; A61B 5/0533; A61B 5/0537; A61B 2562/029
See application file for complete search history.

(56) References Cited

U.S. PATENT DOCUMENTS

| 2013/0041235 A1* | 2/2013 | Rogers | A61B 5/6867 600/306 |
|---|---|---|---|
| 2014/0330088 A1* | 11/2014 | Libbus | A61B 5/0002 600/301 |
| 2016/0192501 A1* | 6/2016 | Yan | H01L 29/0673 29/846 |

* cited by examiner

*Primary Examiner* — Eun Hwa Kim
(74) *Attorney, Agent, or Firm* — Thomas | Horstemeyer, LLP

(57) ABSTRACT

Disclosed are various embodiments for a flexible hydration sensor that can be implemented in a wearable device. A hydration monitoring device can include at least one flexible electrode comprising a plurality of silver nanowires embedded within a polydimethylsiloxane (PDMS) substrate. Processing circuitry can be configured to measure a hydration level of an individual wearing the hydration monitoring device based at least in part on a measurement of a skin impedance of the individual. In some embodiments, the hydration monitoring device can also generate a hydration metric based on the level of hydration and display the hydration metric.

20 Claims, 15 Drawing Sheets

PERSONAL HYDRATION MONITOR

CROSS REFERENCE TO RELATED APPLICATIONS

This application claims the benefit of U.S. Provisional Application No. 62/164,154, filed May 20, 2015, the entire contents of which is hereby incorporated herein by reference.

GOVERNMENT RIGHTS NOTICE

This invention was made with government support under grant number EEC-1160483, awarded by the National Science Foundation (NSF). The government has certain rights in the invention.

BACKGROUND

Hydration of the body is an important physiological parameter to measure, but is hard to measure accurately. For example, high performance athletes would like to know more about their hydration state since this can be directly linked to athletic performance. Such knowledge is also of interest to workers such as first responders who may dehydrate when working in extreme conditions. It is a well-known problem that, when coaches start training young athletes for football in the summer and the military starts physically training recruits, that dehydration and heat stroke pose serious risks.

Proper hydration in humans and animals is required to regulate body temperature, blood pressure, heart rate, etc. Currently, accurate hydration testing equipment is not readily available to the masses. Instead, it requires heavy and bulky laboratory equipment for processing samples, such as urine or blood. While some mobile hydration monitors have been developed, some employ invasive technologies, such as microscopic needles that puncture the skin to measure hydration through the presence of interstitial fluid. Other methods measure the skin impedance using metal electrodes in a fixed geometry. Less invasive hydration monitors rely on an analysis of chemicals produced in sweat. These monitors measure sodium and chloride levels in sweat. However, if a person is not producing sweat, these types of hydration monitors are ineffective.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

Figure 1:
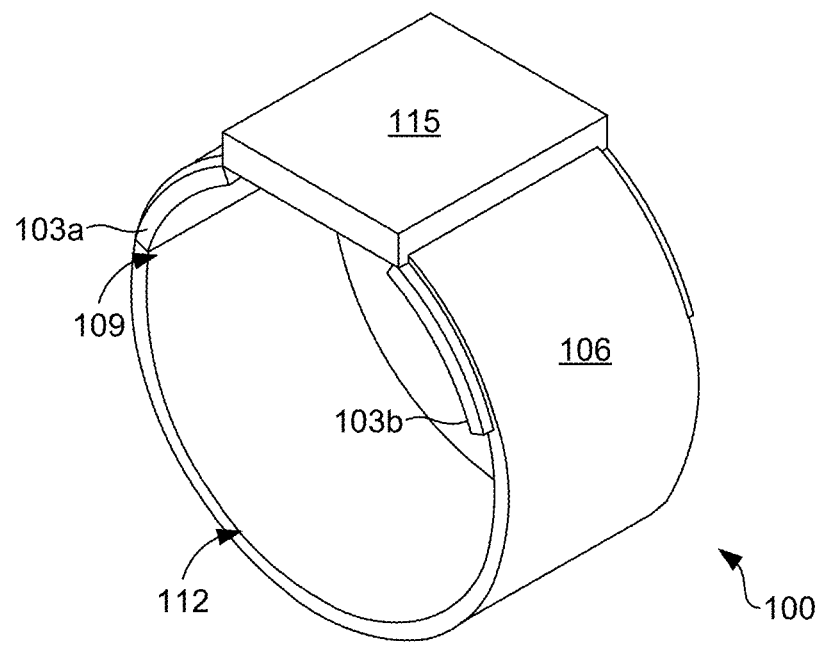
FIG. 1 illustrates an example wearable hydration monitor comprising one or more hydration sensing electrodes according to various embodiments.

As noted above, proper hydration in humans and animals is required to regulate body temperature, blood pressure, heart rate, etc. Many methods to assess dehydration are qualitative, for example, by accessing how the person looks (e.g., sunken eyes and cracked lips) or examining the volume and color of urine. More quantitative assessment relies on measuring change in hydration by weighing an individual before and after exercise, or by using instruments that measure the physical properties of the skin such as conductance, capacitance, impedance, thermal conductivity, and reflectance of optical or electromagnetic radiation. Almost all of these measurements are taken in clinical settings.

To replace the expensive, bulky instruments and achieve low cost, wearable, long-term hydration monitoring, wearable hydration sensors that are mechanically compliant and can form a conformal contact with the skin would represent a significant technological advance. Mechanical compliance can facilitate the long-term wearability of the sensors and allows for spatially mapping the electronic properties of the skin by using an array of sensors 5 Ultrathin "electronic tattoo" 6, 7 is a representative example, which adopts the top-down approach (i.e. patterning followed by transfer printing) to enable high-performance stretchable electronics.

According to various embodiments, wearable hydration monitor (also referred to as a hydration monitoring device) can include a flexible electrode on a flexible substrate. In some embodiments, the flexible electrode includes a plurality of conductive nanowires or carbon nanotubes arranged in a polymer matrix. The polymer matrix can be embodied as a polymeric organosilicon compound, such as polydimethylsiloxane (PDMS), another flexible polymer or silicone, or combinations thereof. The wearable hydration monitor can further include processing circuitry configured to measure the level of hydration of an individual (e.g., human) wearing the hydration monitor using a skin impedance measurement obtained by the electrode. In some embodiments, the wearable hydration monitor can further include a battery, such as a coin cell battery or other suitable battery, to power the electrode and/or the processing circuitry. The conductive nanowires (e.g., silver nanowires, AgNWs) can be embedded in a PDMS substrate as further described herein.

As a more particular example of an embodiment, a wearable skin hydration sensor in the form of a flexible electrode capacitor is described. A level of hydration can be determined based on an impedance measurement of skin taken using the flexible electrode capacitor. The flexible electrode capacitor can include two interdigitated or parallel electrodes made of silver nanowires in a PDMS matrix or substrate. The stretchable nature of the AgNW/PDMS electrode allows robust contact and provides a conformal mechanical and electrical interface to the skin. The hydration sensor is insensitive to external humidity change and, as described herein, can be calibrated against a commercial skin hydration system over a wide hydration range. The hydration sensor can be packaged into a flexible wristband, together with a network analyzer chip, a button cell battery, and an ultralow power microprocessor with a radio transceiver.

In other embodiments, the wearable skin hydration sensor can be embodied as a multifunctional sensor patch including a strain sensor, electrocardiography or biopotential electrodes, and a skin hydration sensor for multimodal sensing. The wearable wristband, chest patch, etc. can be used for low cost, wireless and continuous sensing of skin hydration and other health parameters.

The conformal nature of the flexible electrodes described herein allow reproducible contact with an individual's skin under a variety of conditions. As compared to a various commercially-available systems, the wearable hydration monitor described herein exhibits good accuracy during experiments with artificial and human skin. Because it is wearable, the hydration monitor can be used in several situations where dehydration can be a safety risk or where people work or train in extreme conditions. Although an embodiment described herein describes the hydration monitor as being worn on the wrist, hydration measurements can also be made by having the electrodes placed in contact with the face, arm, torso, legs, or other parts of the body. In these cases, the method of making contact to the body can be by holding the device in contact by hand, by use of a strap, a patch, or other methods.

In the following paragraphs, a general description of the system and its components is provided, followed by a discussion of the operation of the same.

With reference to FIG. 1, an example monitoring device 100 comprising one or more hydration sensing electrodes is illustrated. The monitoring device 100 can be worn around the wrist, arm, leg, ankle, or other suitable location on a individual or animal, for example, to measure a level of hydration and/or sweat rate of the individual. In various embodiments, the monitoring device 100 includes a first electrode 103a and a second electrode 103b configured to measure skin impedance. As described in greater detail below, the first electrode 103a and/or the second electrode 103b (collectively "the electrodes 103") can be embodied as silver nanowires embedded in PDMS, thereby creating a conductive and flexible electrode 103.

In some embodiments, the electrodes 103 are located at an interior of a wrist band 106, such that they make direct or indirect contact with skin. To this end, in some embodiments, the electrodes 103 are positioned in an upper portion 109 of the wrist band 106. However, in alternative embodiments, the electrodes 103 can be positioned in a lower portion 112 of the wrist band 106. The first electrode 103a and/or the second electrode 103b can be positioned beneath or on a bottom side of a housing 115, which can enclose various components of the monitoring device 100.

The monitoring device 100 can include low power network analyzer circuitry to measure impedance as described herein. The low power network analyzer circuitry can be operable to measure impedance between about 10 kHz and 100 kHz or, in some cases, impedance below 10 kHz or above 100 kHz. Further, the monitoring device 100 can comprise a low or ultra-low voltage processor. In some embodiments, the monitoring device 100 includes a Bluetooth® radio physical layer transceiver, associated antenna, and interface circuitry to communicate impedance measurements or other metrics and data derived from the impedance measurements. The measurements can be communicated to external devices, such as smartphones, smartwatches, laptop computing devices, tablet computing devices, etc. In some cases, the Bluetooth® transceiver and/or antenna can be placed within or integrated with the wrist band 106. Although described as utilizing Bluetooth®, other communications standards can be employed, such as near field communication (NFC), Z-Wave®, ZigBee®, wireless infrared, ultra wideband, wireless induction, etc.

Although described as a wrist band 106, other suitable bands can be employed to hold, position, and/or maintain components of the monitoring device 100 against various areas of the skin of an individual or animal. Additionally, power to the various electrical components of the monitoring device 100 can be supplied by a battery, such as a coin cell battery or other suitable battery. The battery and/or the other components described herein can be positioned within the housing 115, for example, or at any other suitable location. In various embodiments, the housing 115 can further include a display (not shown) which can render skin impedance measurements or metrics derived therefrom. The display can include, for example, one or more devices such as liquid crystal display (LCD) displays, gas plasma-based flat panel displays, organic light emitting diode (OLED) displays, electrophoretic ink (E-ink) displays, LCD projectors, other types of display devices, etc.

Figure 2:
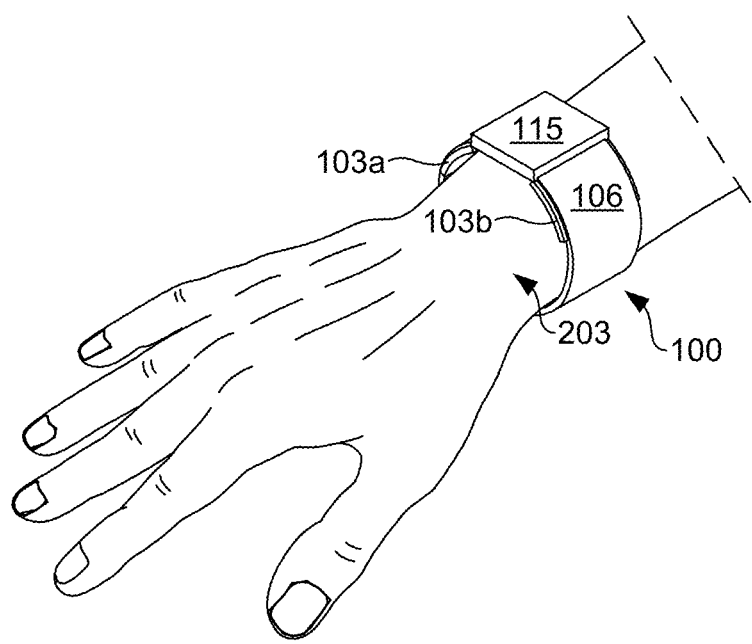
FIG. 2 is another illustration of the wearable hydration monitor shown in FIG. 1 according to various embodiments.

FIG. 2 is another illustration of the monitoring device 100 shown in FIG. 1. In FIG. 2, the hydration monitor 100 is worn around an individual's wrist 203, for example, to measure the hydration of the individual. The first electrode 103a and/or the second electrode 103b including, for example, silver nanowires embedded in PDMS, are located at an interior of a wrist band 106, such that they make direct contact with skin of the individual. In the example shown in FIG. 2, the electrodes 103 are positioned in an upper portion 109 of the wrist band 106 to touch a top portion of the wrist 203. However, in alternative embodiments, the electrodes 103 can be positioned in a lower portion 112 of the wrist band 106 to make contact with the middle or lower parts of the wrist 203. The wrist band 106 can be maintained about the wrist 203 using a fastener, such as a clasp, a buckle, magnet, Velcro®, or other suitable fastener.

Figure 3:
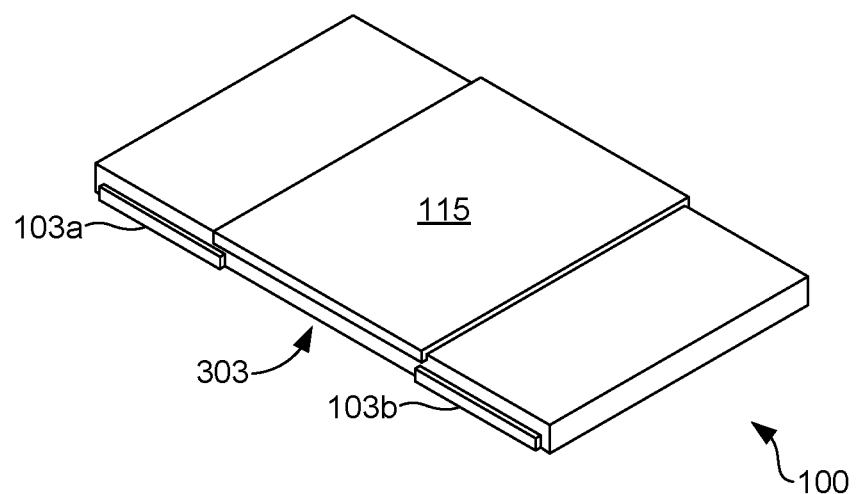
FIG. 3 illustrates another example of a wearable hydration monitor comprising multiple flexible hydration sensing electrodes according to various embodiments.

Referring next to FIG. 3, another example of the monitoring device 100 is shown. In FIG. 3, the hydration monitor 100 can be embodied as a patch that can be worn at a suitable body location, for example, to measure the hydration of the wearer. Again, the electrodes 103 can include silver nanowires embedded in PDMS, creating conductive and flexible electrodes that can move and bend while retaining position on the wearer. A bottom side 303 of the monitoring device 100 can include a suitable adhesive for attaching to skin of the wearer.

As described above, the monitoring device 100 implemented in a patch can include low power network analyzer circuitry to measure impedance. In various embodiments, the low power network analyzer circuitry can be operable to measure impedance between 10 kHz and 100 kHz or, in some cases, impedance below 10 kHz or above 100 kHz. Further, the monitoring device 100 can include a low or ultra-low voltage processor. In some embodiments, the monitoring device 100 includes a Bluetooth® transceiver and antenna to communicate impedance measurements, metrics, and other data derived from the impedance measurements, to external devices, such as smartphones, smartwatches, laptop computing devices, tablet computing devices, etc.

A coin cell or other suitable battery can provide power to the electrical or circuit components of the monitoring device 100. The battery and/or the other components described herein can be positioned within the housing 115 or at any other suitable location.

Figure 4:
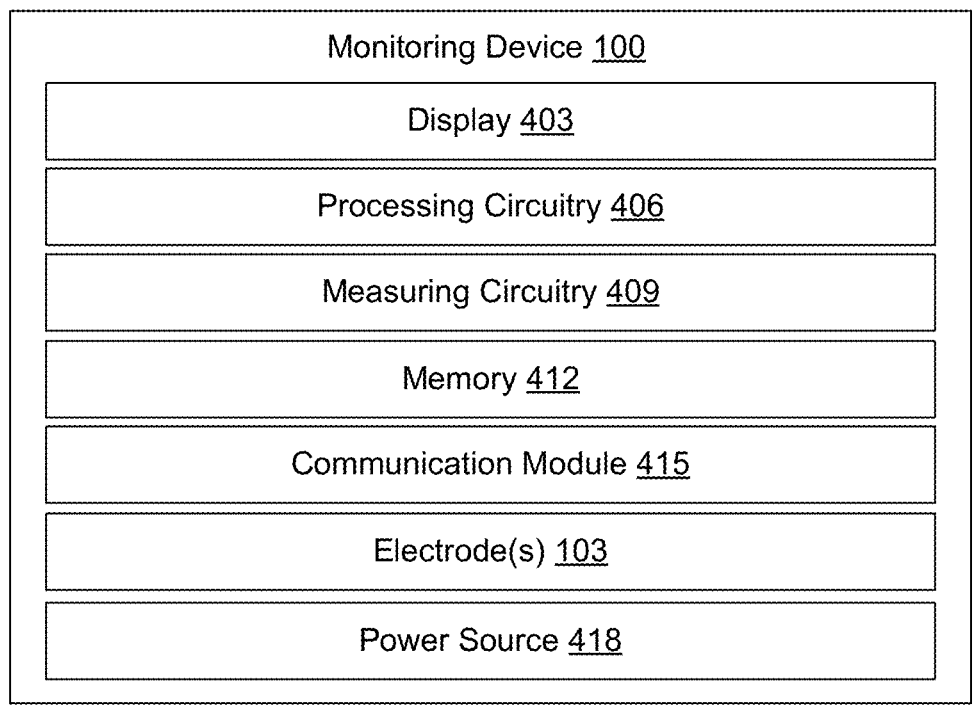
FIG. 4 illustrates a schematic block diagram of processing modules in a wearable hydration monitor according to various embodiments.

FIG. 4 illustrates a schematic block diagram of processing modules in the monitoring device 100 according to various embodiments. The monitoring device 100 can include a display 403, processing circuitry 406, measuring circuitry 409, memory 412, communication module 415, one or more electrodes 103, and power source 418. The display 403 can include, for example, one or more devices such as liquid crystal display (LCD) displays, gas plasma-based flat panel displays, organic light emitting diode (OLED) displays, electrophoretic ink (E-ink) displays, other types of display devices, etc.

The processing circuitry 406 can be embodied as a combination of one or more processing circuits, processors, embedded application-specific circuitry modules, system-on-chip (SOC) microcontrollers, and/or other suitable processing circuitry. The processing circuitry 406 is configured, in part through the execution of computer-readable instructions, to obtain measurements from the measuring circuitry 409, perform computations on the measurements, and/or send the measurements to other devices via the communication module 415. As one example, the processing circuitry 406 can be embodied as an ultra-low power MSP430® microcontroller and/or the CC2541 2.4-GHz Bluetooth® low energy and Proprietary System-on-Chip manufactured by Texas Instruments®. In that context, it can be appreciated that the components of the processing circuitry 406 can include low voltage or ultra-low voltage components.

The measuring circuitry 409 can include a combination of one or more impedance measuring or processing circuits, such as embedded network analyzers, embedded impedance converter network analyzers, or other devices configured to measure impedance, biopotential, and other metrics described herein using the electrodes 103. The measuring circuitry 409 can be operable to measure impedance between 10 kHz and 100 kHz or, in some embodiments, impedance above 10 kHz. To this end, the measuring circuitry 409 can be embodied as an AD5933 impedance network analyzer manufactured by Analog Devices®. In that context, the measuring circuitry 409 can be configured to present an excitation frequency to the complex impedance of the electrodes 103, sample a response of the complex impedance to the excitation frequency, and measure a level of hydration using the flexible electrode based on the response.

The memory 412 can include volatile and/or nonvolatile memory and data storage components for storing measurements obtained by the measuring circuitry 409, program instructions, other data, and/or or executable software. Thus, the memory 412 can include, for example, random access memory (RAM), read-only memory (ROM), hard disk drives, solid-state drives, USB flash drives, memory cards, and/or other memory components, or a combination thereof. In addition, the RAM can include, for example, static random access memory (SRAM), dynamic random access memory (DRAM), magnetic random access memory (MRAM), and other related devices. The ROM can include, for example, a programmable read-only memory (PROM), an erasable programmable read-only memory (EPROM), an electrically erasable programmable read-only memory (EEPROM), or other related devices.

The communication module 415 can include a Bluetooth® transceiver and/or antenna, although other communication mediums can be employed in addition to or in lieu of Bluetooth®, such as NFC, Z-Wave®, ZigBee®, wireless infrared, ultra wideband, wireless induction, etc. As one example, the communication module 415 can be embodied as the CC2541 2.4-GHz Bluetooth® low energy and Proprietary System-on-Chip manufactured by Texas Instruments®.

The electrodes 103 can be embodied as conductive nanowires (e.g., silver nanowires) embedded within a flexible substrate, such as PDMS, another flexible polymer or silicone, or combinations thereof. As PDMS is a flexible substrate, the electrodes 103 can be both conductive and flexible, allowing the electrodes 103 and/or the monitoring device 100 to retain its position on the wearer. The power source 418 can be embodied as rechargeable or non-rechargeable battery or battery cell, such as an alkaline, lithium-ion, nickel-cadmium battery, or other suitable type of battery. In some embodiments, the power source 418 can include a coin cell battery.

Figure 5:
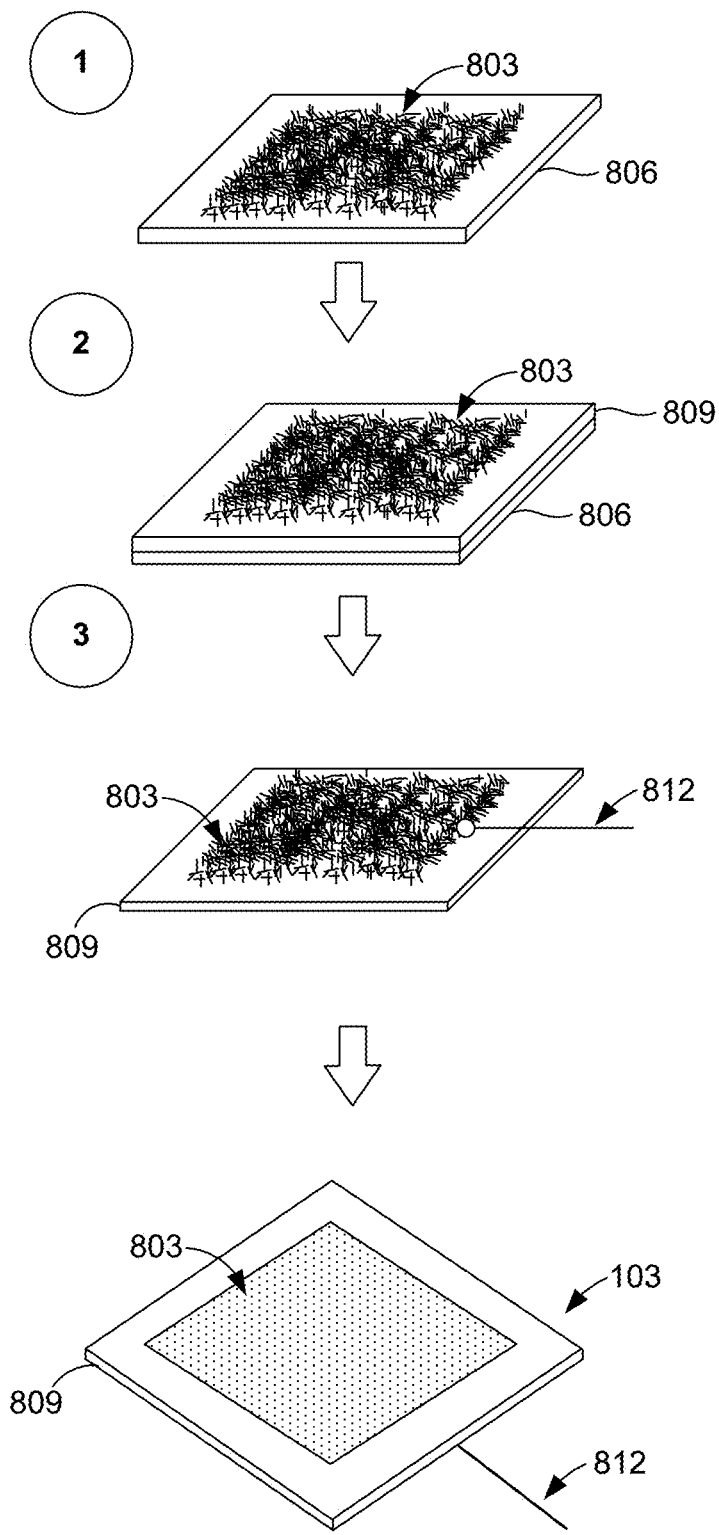
FIG. 5 illustrates an example of fabricating an electrode for a wearable hydration monitor according to various embodiments.

FIG. 5 illustrates an example of fabricating an electrode for a wearable hydration monitor according to various embodiments. Starting with step 1, a solution comprising nanowires 803, such as silver nanowires, is casted onto a substrate 806, for example, in a predefined arrangement. In the example of FIG. 5, a nanowire solution can be casted on the substrate such that a uniform layer of nanowires is created. In various embodiments, the substrate can include silicon, plastic, glass, a combination thereof, or any other suitable substrate material. The solution of nanowires 803 on the substrate 806 is dried such that liquid from the nanowire solution evaporates. As a result, a network of nanowires 803 on the substrate 806 remains in the predefined arrangement.

In step 2, a polymeric organosilicon compound, such as PDMS, is poured over the nanowires to create a mixture of nanowires and PDMS (mixture 809). As can be appreciated, the liquid PDMS is poured to avoid changing or otherwise interfering with the arrangement of the nanowires 803. PDMS can be categorized as a polymeric organosilicon compound often referred to as silicones. The polymeric organosilicon compound can be selected for its rheological properties. PDMS is optically clear, and, in general, inert, non-toxic, and non-flammable. It is also called dimethicone and is one of several types of silicone oil (polymerized siloxane). Its applications range from contact lenses and medical devices to elastomers; it is also present in shampoos (as dimethicone makes hair shiny and slippery), food (antifoaming agent), caulking, lubricants, kinetic sand, and heat-resistant tiles.

Next, in step 3, one or more conductive elements 812, such as a copper lead wire, are pressed on top of the mixture 809 before it has dried or cured. The conductive elements can be electrically connected to the measuring circuitry 409 and/or the processing circuitry 406. The mixture 809 can be heated at a suitable temperature for a suitable amount of time to cure the PDMS. Once cured, the mixture 809 is peeled off of the substrate 806, after which the nanowires 803 are visibly bonded into to the PDMS and the one or more conductive elements 812 are securely connected to the nanowires. The result is an electrode 103 having a uniform network of nanowires 803 capable of bending and flexing.

Figure 6:
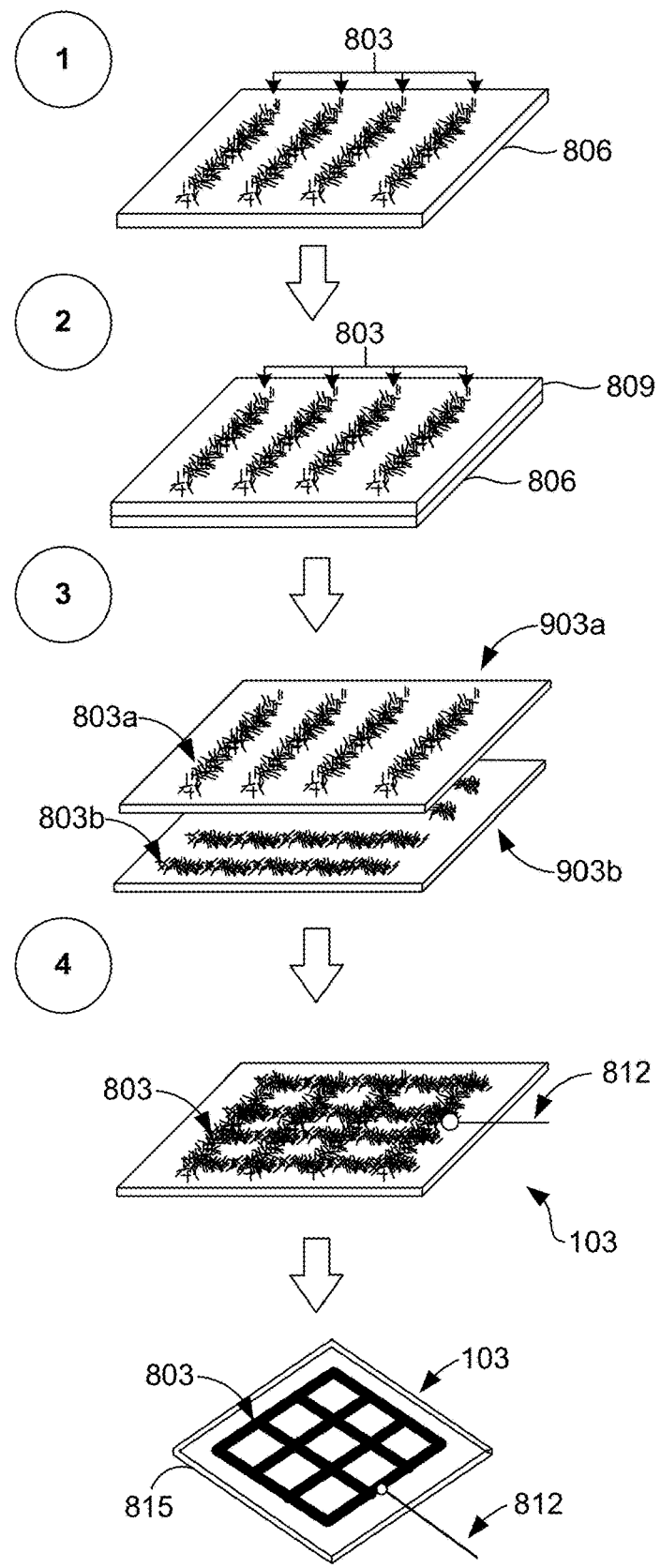
FIG. 6 illustrates another example of fabricating an electrode for a wearable hydration monitor according to various embodiments.

FIG. 6 illustrates another example of fabricating an electrode for a wearable hydration monitor. Starting with step 1, a solution comprising nanowires 803, such as silver nanowires, are casted onto a substrate 806, for example, in a predefined arrangement. In the example of FIG. 6, the solution of nanowires 803 is caste into a number of parallel rows on the substrate 806. The substrate 806 can include silicon, plastic, glass, a combination thereof, or any other suitable substrate material. The solution of nanowires 803 is dried on the substrate 806 such that liquid from the nanowire solution evaporates. As a result, a network of nanowires 803 on the substrate 806 remains in the predefined arrangement.

In step 2, liquid PDMS is poured over the nanowires to create a mixture 809 of nanowires and PDMS. The liquid PDMS is poured to avoid changing or otherwise interfering with the arrangement of the nanowires 803. In steps 3 and 4, the mixture 809 can be heated at a suitable temperature for a suitable amount of time to cure the PDMS. The cured PDMS is peeled off of the substrate 806, after which the network of nanowires is visibly bonded to the PDMS and the one or more conductive elements 812 (e.g., copper lead wires) are securely connected to the nanowire network. Two or more layers 903a, 903b, etc. (collectively layers 903) can be combined such that a matrix of nanowires 803a, 803b, etc. can be formed having the first arrangement of nanowires 803a in cured PDMS and the second arrangement of nanowires 803b in cured PDMS. As can be appreciated, other arrangement and/or patterns of nanowires can be realized.

One or more conductive elements 812, such as copper lead wires, can be pressed on top of the nanowire PDMS mixture before the nanowire PDMS mixture has dried or cured. In various embodiments, the one or more conductive elements can be configured to operatively connect to the measuring circuitry 409 and/or the processing circuitry 406. The result is an electrode 103 having a uniform network of nanowires 803 capable of bending and flexing. In the skin hydration sensors described herein, AgNWs can be embedded just below the surface of the PDMS.

Figure 7A:
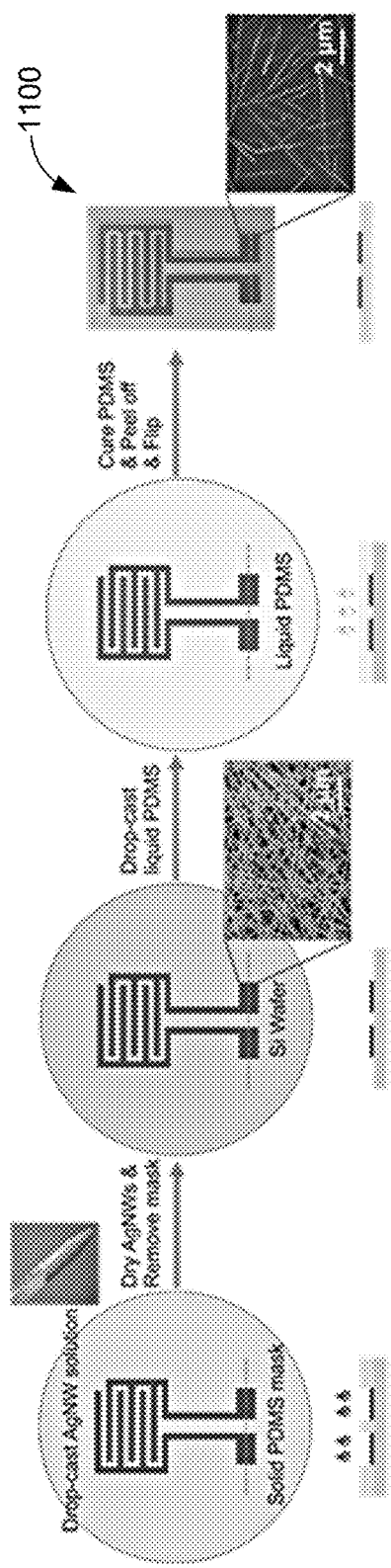
FIG. 7A illustrates another example of fabricating an electrode according to various embodiments.

Turning to other embodiments, FIG. 7A illustrates another example of fabricating an electrode 1100. Due to the good conductivity of silver and the mechanical robustness of nanomaterials and polymers, stretchable conductors which can maintain good conductivity at highly strained state (conductivity of ~5000 S/cm at 50% tensile strain) can be achieved in the manner shown in FIG. 7A. As shown to the far left, AgNWs were cast in an interdigitated pattern with finger length of above 20 mm and spacing of above 2 mm, although other sizes are with the scope of the embodiments. The AgNWs were then drop cast into and embedded just below the surface of liquid PDMS, as shown in the second frame from the left, to form two stretchable, interdigitated electrodes.

More particularly, from left to right in FIG. 7A, liquid PDMS, such as Sylgard® 184, by Dow Corning Corporation, with the weight ratio of "base" to "curing agent" of about 10:1 was cast onto a Si substrate, degassed in a vacuum chamber and cured at 60° C. for 2 hours. The cured PDMS was patterned into an interdigitated shape with finger length of 20 mm and spacing of 2 mm. AgNWs in ethanol (e.g., SLV-NW-90, Blue Nano) with average length and diameter of 10 μm and 90 nm were drop cast into the area defined by the mask. The solvent was then evaporated with a temperature of 50° C. After removing the PDMS mask, AgNWs patterns were formed on the substrate. Next, liquid PDMS was cast on top of the AgNW pattern, degassed, and cured at 60° C. for 2 hours. The patterned AgNWs were embedded just below the PDMS surface when it was peeled off the Si substrate. Conductive paste was finally applied onto the two ends of the AgNW/PDMS sensor to interconnect with other components. This process is described as an example, and other types of PDMS, other cure times, and other cure temperatures, among other variables, can be applied to fabricating electrodes similar to the electrode 1100.

Interdigitated electrode patterns were chosen to maximize the interaction between the two electrodes within a small area and measure skin hydration. The two contact pads at the bottom of the electrode are used to connect the hydration sensor to other circuit components. The resulting electrode 1100 is stretchable and mechanically/electrically robust, which allows for long-term use. In addition, the stretchable nature of the electrode 1100 enables conformal contact with the surface of the skin that is generally rough.

Figure 7B:
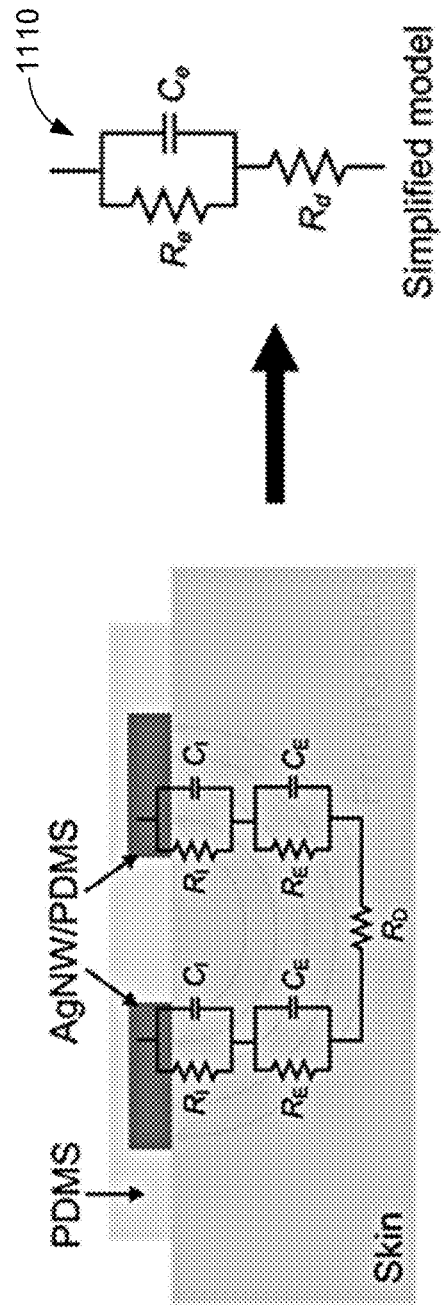
FIG. 7B illustrates a representative example of an electrode placed the skin a fringing field penetrating the upper layer of skin, along with the equivalent electrode-skin and simplified model, according to various embodiments.

FIG. 7B illustrates a representative example of an electrode placed the skin a fringing field penetrating the upper layer of skin, along with the equivalent electrode-skin and simplified model, according to various embodiments. Skin impedance is a commonly used method to measure skin hydration and is achieved by placing two electrodes on the surface of the skin. The fringing field between the two electrodes penetrates the upper layer of skin, as schematically shown in FIG. 7B. The skin impedance measured by the two electrodes can be electrically modeled using a series of capacitors and resistors as shown. The contact interface between electrode and the skin surface can be described by a resistor $R_I$ in parallel with a capacitor $C_I$, which is dependent on applied pressure and the humidity of the skin. The epidermis is modeled by a parallel circuit consisting of a capacitor $C_E$ and a resistor $R_E$. The dermis and underlying subcutaneous tissues, mainly composed of blood vessels, nerves, preparatory glands and hair follicles, exhibits a pure resistive behavior and can be modeled by a resistor $R_D$.

Due to symmetry of the two electrodes, the equivalent circuit 1110 can be approximated as a parallelly connected resistor $R_e$ and capacitor $C_e$ arising from the electrode-skin contact interface and epidermis, in series with a resistor $R_d$ from the dermis and the underlying tissue. When no pressure is applied on the sensor, increases in water content of skin improves the contact between the electrode and skin by providing more conductive pathways and increases both the conductivity and dielectric constant of the skin. The decreased contact impedance and decreased impedance from the epidermis result in a decrease of the measured skin impedance as a function of skin hydration level.

The sensing frequency between the two electrodes determine the sensitivity and the depth of the skin being interrogated. Understanding the penetration depth of the electric field allows some separation of changes in impedance due to sweat on the surface and the hydration of the stratum corneum layer. At lower frequencies, such as between about 0.1-1000 Hz, for example, the α relaxation response is mainly due to the topmost layer of skin. The stratum corneum. β relaxation, between the higher frequencies of about 100 kHz and 500 MHz, relates to the polarization of the water content of macromolecules. The γ relaxation at the even higher frequency range, between about 3-30 GHz, correlates to the vibration of free water molecules in the tissue. Considering these reasons and the maximum frequency (e.g., 100 kHz) limitations of certain network analyzers, the working frequency range of the skin hydration sensors described herein can be selected in the range of about 10-100 kHz, for example, to ensure a good sensitivity and avoid the influence of the hydration change in the topmost layer of skin.

The skin hydration sensors were characterized by three different tests to evaluate the effect of the ambient hydration or humidity, and the skin hydration using both artificial skin and human skin. In other words, the sensor response to external (ambient) and internal (physiological) water content was investigated. The first test investigated the effect of the ambient relative humidity on the skin impedance of the hydration sensor. Artificial skin with similar electrical properties to the upper layers of human skin was fabricated and optimized for low frequency sensing. The artificial skin served as a control in the sense that its own water content remained constant throughout the test to ensure that any change in the measured impedance was a result of the varying external humidity.

The hydration sensor was placed on the artificial skin and inserted into a humidity chamber. The humidity was lowered to 20% relative humidity by flooding the chamber with nitrogen gas. From there, the intake of nitrogen was adjusted to allow the humidity to slowly increase over a period of approximately 60 min, which allowed the humidity levels to stabilize at each interval while being fast enough to prevent any water evaporation from the artificial skin. An impedance measurement at 10 kHz was recorded at a 5% humidity increase interval. At approximately 45% relative humidity, a bubbler was used to continue increasing the humidity up to 100% relative humidity.

Figure 8A:
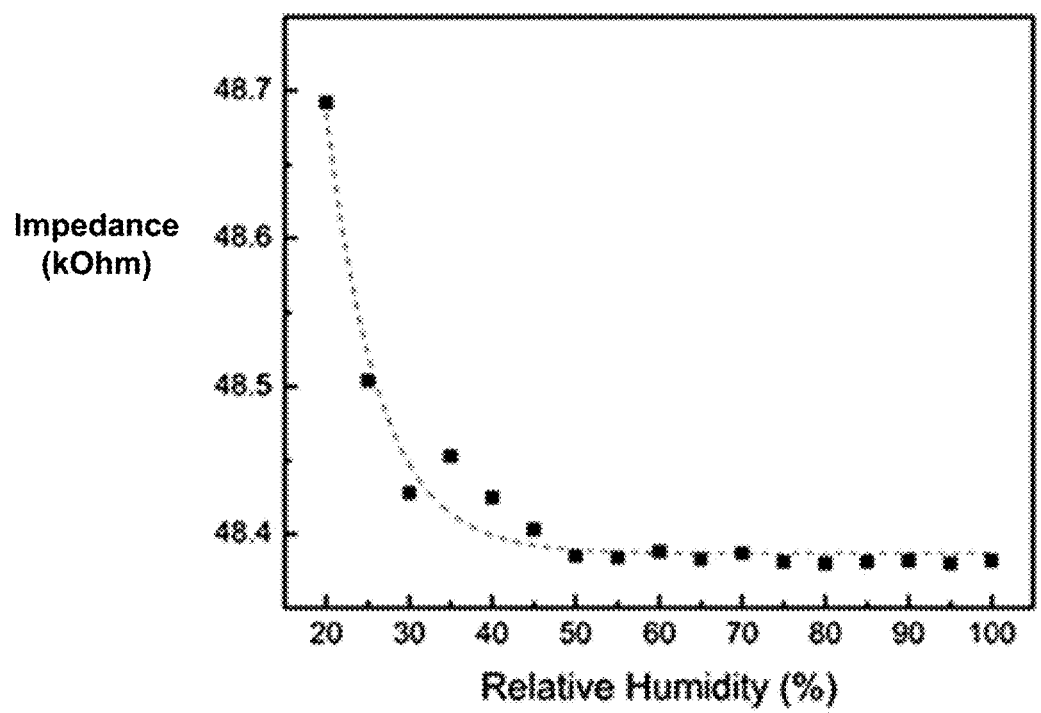
FIG. 8A illustrates impedance values measured from an electrode on artificial skin as a function of increasing humidity according to various embodiments.

During the test, the temperature of the humidity chamber was 20±0.5° C. The results, depicted in FIG. 8A, show a 0.62% change in impedance readings with increasing relative humidity levels. This indicates that the skin hydration sensor can give stable readings regardless of the external environment of the wearer. It also demonstrates the robust contact of the hydration sensor with the skin.

Figure 8B:
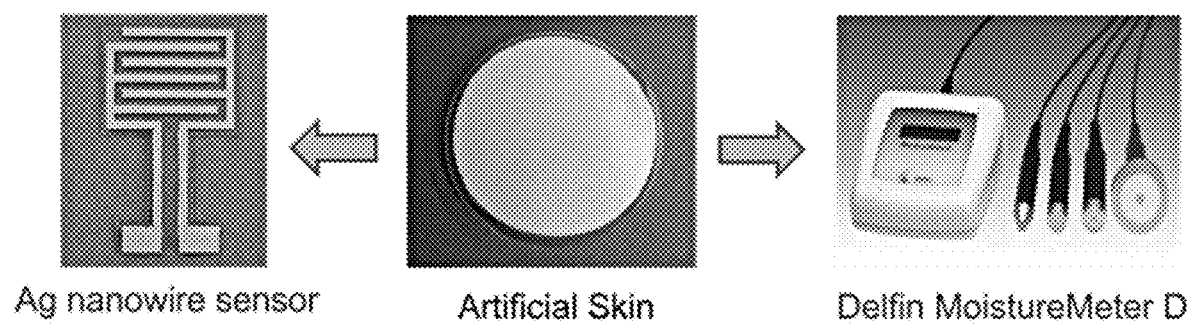
FIG. 8B illustrates an example calibration conducted on artificial skin between an electrode and a commercial moisture meter according to various embodiments.

The second test investigated the effect of the internal water content, or the skin hydration level, on the skin impedance using an artificial skin as a control. This test also served as a calibration of the skin hydration sensor against a commercially available hydration meter (i.e., a Delfin Tech Moisture Meter D). The moisture meter (MMD) included rigid open-ended coaxial probes, as indicated in FIG. 8B, to measure the dielectric constant of the skin relative to that of the air, and the hydration level is indicated using the relative dielectric constant. The use of the artificial skin allows relatively precise control of the skin hydration level over a wide range.

Figure 8C:
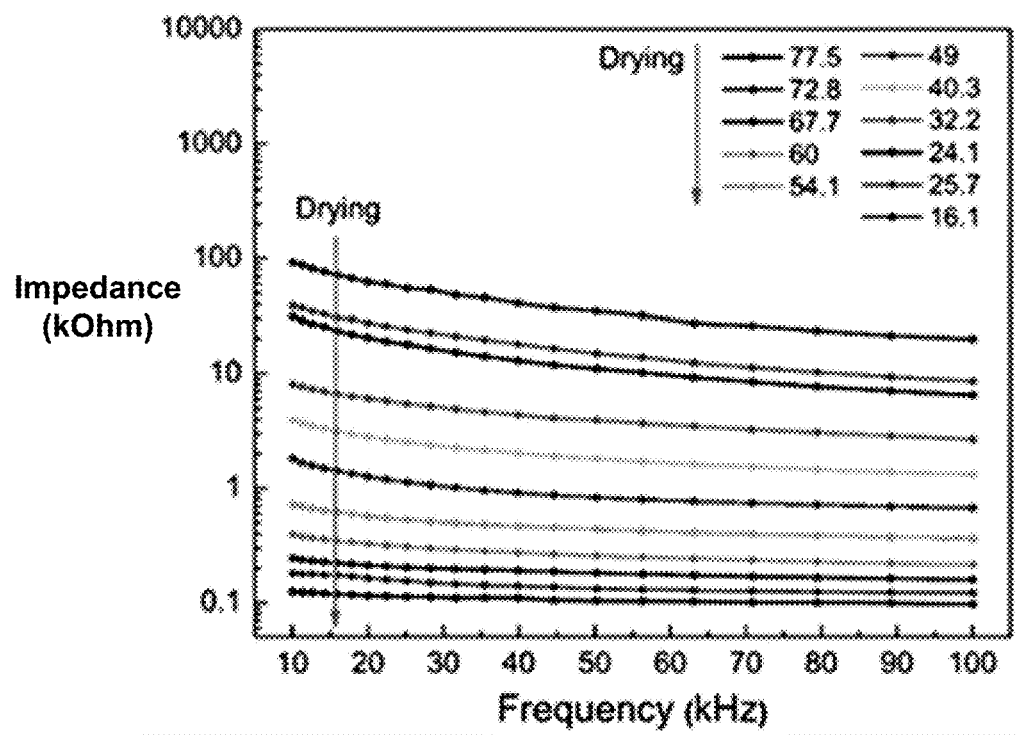
FIG. 8C illustrates example skin impedance measured from an electrode between 10-100 kHz and the corresponding commercial moisture meter readings as the artificial skin dries according to various embodiments.
Figure 8D:
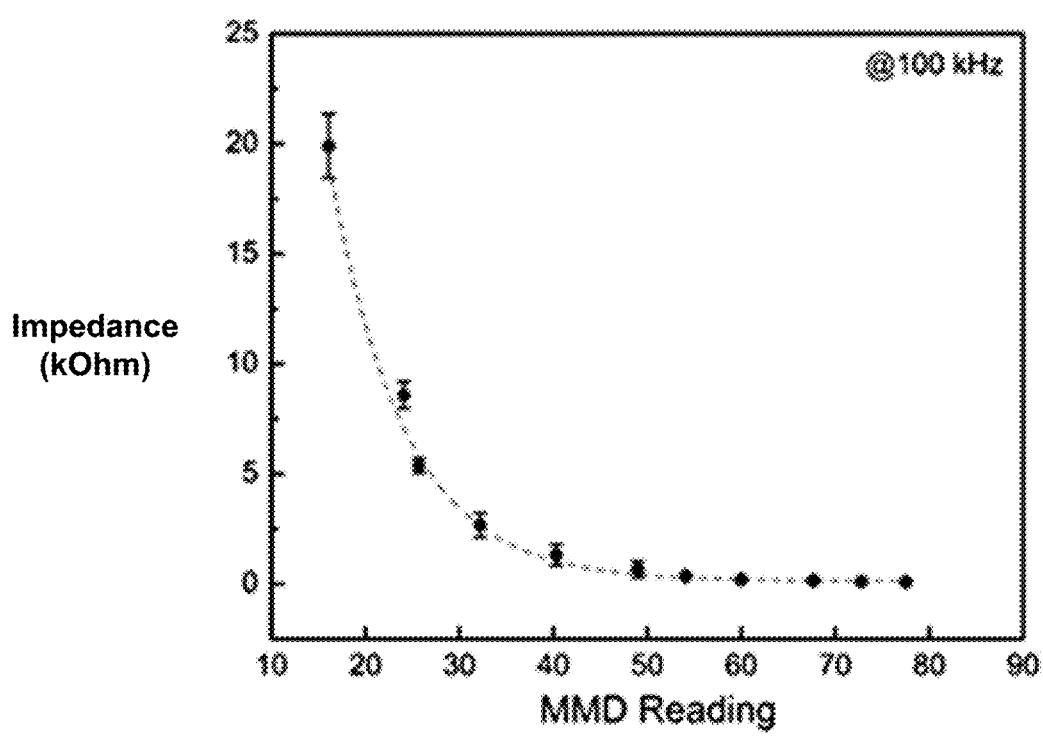
FIG. 8D illustrates an example comparison of skin impedance measured from an electrode between at 100 kHz and the corresponding commercial moisture meter readings as the artificial skin dries according to various embodiments.

In one test, the artificial skin was prepared to be in a relatively highly hydrated state. As the water inside the artificial skin evaporated with the help of a hair dryer, the hydration was measured using both the MMD and the hydration sensor described herein. As expected, the impedance measured by the hydration sensor increased as the water content of the artificial skin decreased, which was correlated with the decrease in the reading of the MMD as shown in FIG. 8C. The relationship between the impedance measured at 100 kHz and the MMD reading also follows an exponential relationship as shown in FIG. 8D.

Figure 8E:
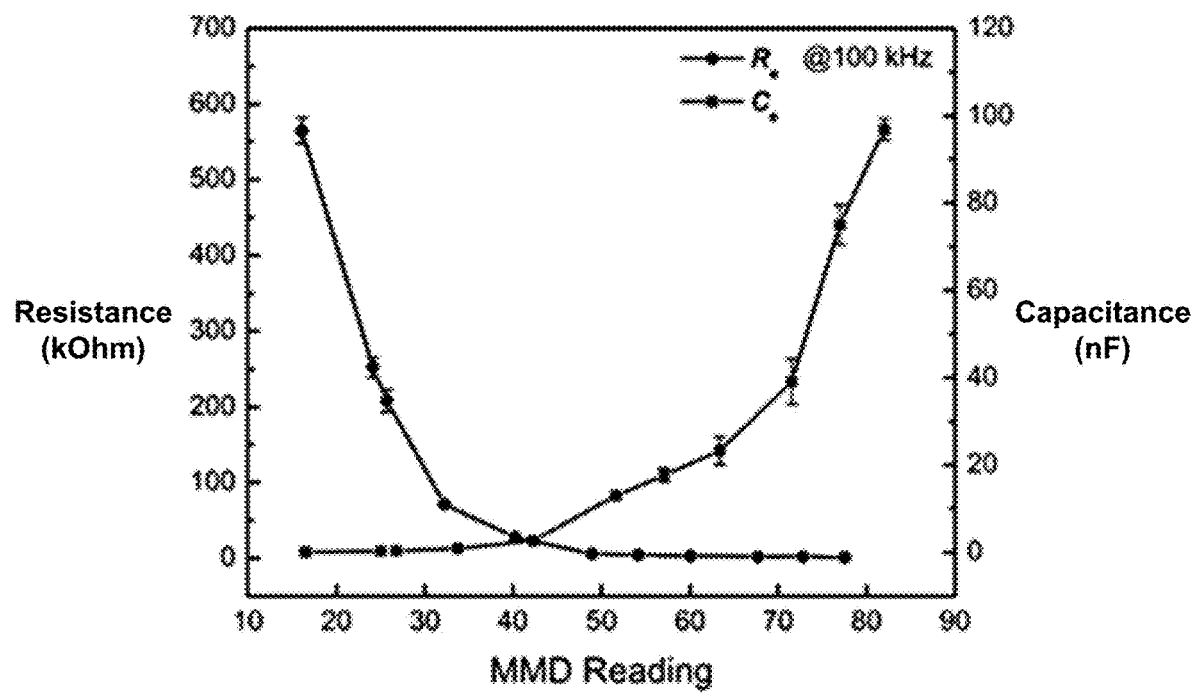
FIG. 8E illustrates curves for extracting equivalent circuit model parameters of skin impedance as a function of commercial moisture meter readings according to various embodiments.

Using this information, Echem Analyst™ software (Gamry Instruments) was employed to extract the equivalent circuit model parameters of the skin impedance. It was found that with the current electrode design and sensing frequency, $R_e$ and $C_e$ play a major role while the value of $R_d$ does not significantly change in the resulting skin impedance. For this reason, only the fitted values of $R_e$ and $C_e$ were summarized, as shown in FIG. 8E. $R_e$ decreases while $C_e$ increases with the increase in the hydration level as a result of improved electrode-skin contact and increased conductivity and dielectric constant of skin.

Figure 9A:
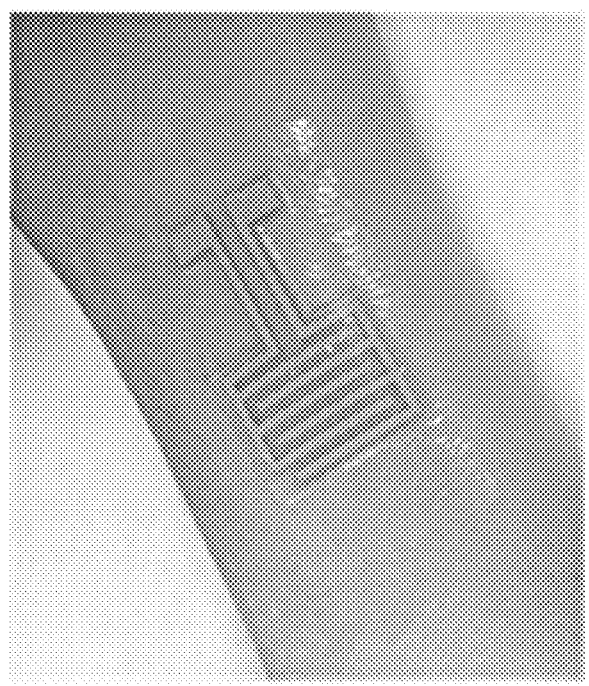
FIG. 9A illustrates a photograph of an example electrode placed on the inner side of a forearm according to various embodiments.
Figure 9B:
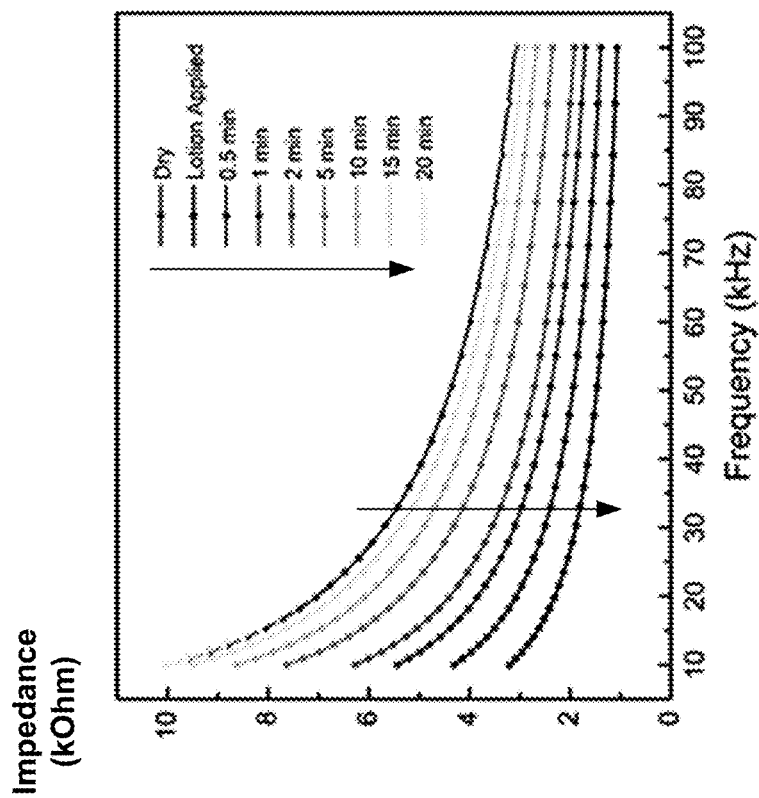
FIG. 9B illustrates a measured impedance change between 10-100 kHz from human skin before and after applying lotion according to various embodiments.
Figure 9D:
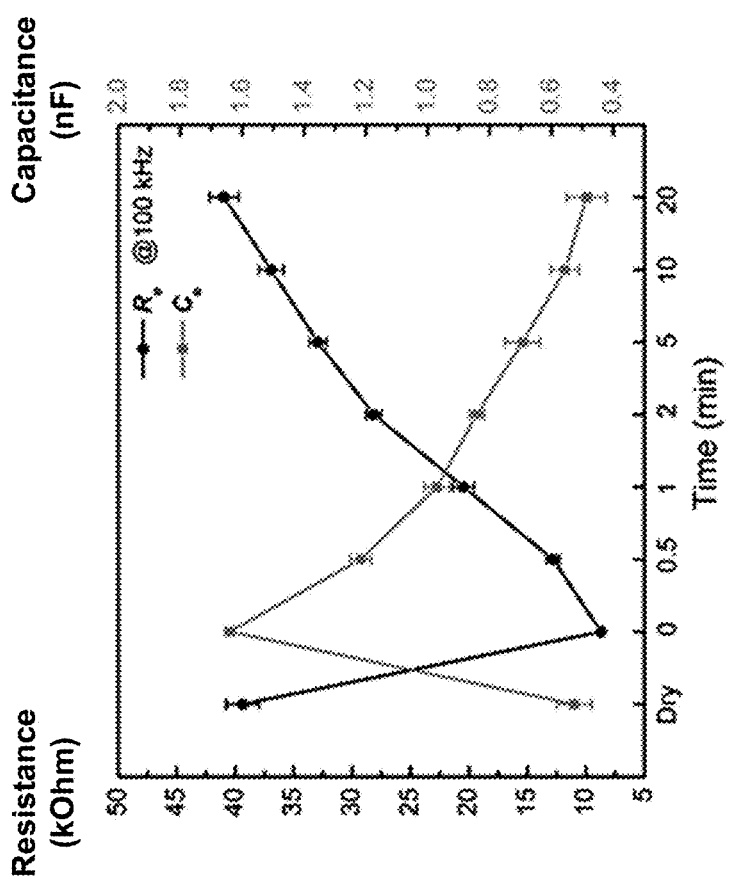
FIG. 9D illustrates curves for extracting equivalent circuit model parameters of skin impedance before and after applying lotion according to various embodiments.
Figure 9C:
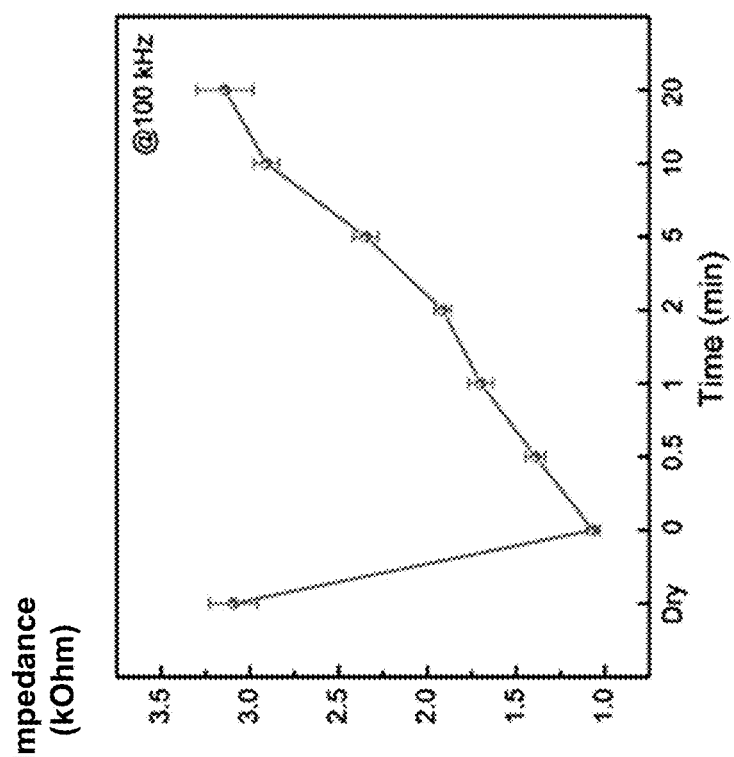
FIG. 9C illustrates a measured impedance change between 10-100 kHz from human skin before and after applying lotion according to various embodiments.

Finally, the hydration sensor was tested with human skin. In that context, FIG. 9A illustrates a photograph of an example hydration sensor electrode placed on the inner side of a forearm of an individual. Skin lotion was applied on the skin of the forearm for 5 min to increase the skin hydration level and then the excess lotion on the skin was removed. Due to the moisturizing effect, a significant drop in skin impedance was observed in the initial reading after applying lotion as shown in FIGS. 9B and 9C, corresponding to an increase in skin hydration. The skin impedance slowly recovered with time and fully recovered to the value before applying lotion after 20 min. Consistently, $R_e$ showed a similar trend with skin impedance and $C_e$ showed an opposite trend as shown in FIG. 9D, which is consistent with the previous analysis.

Figure 10A:
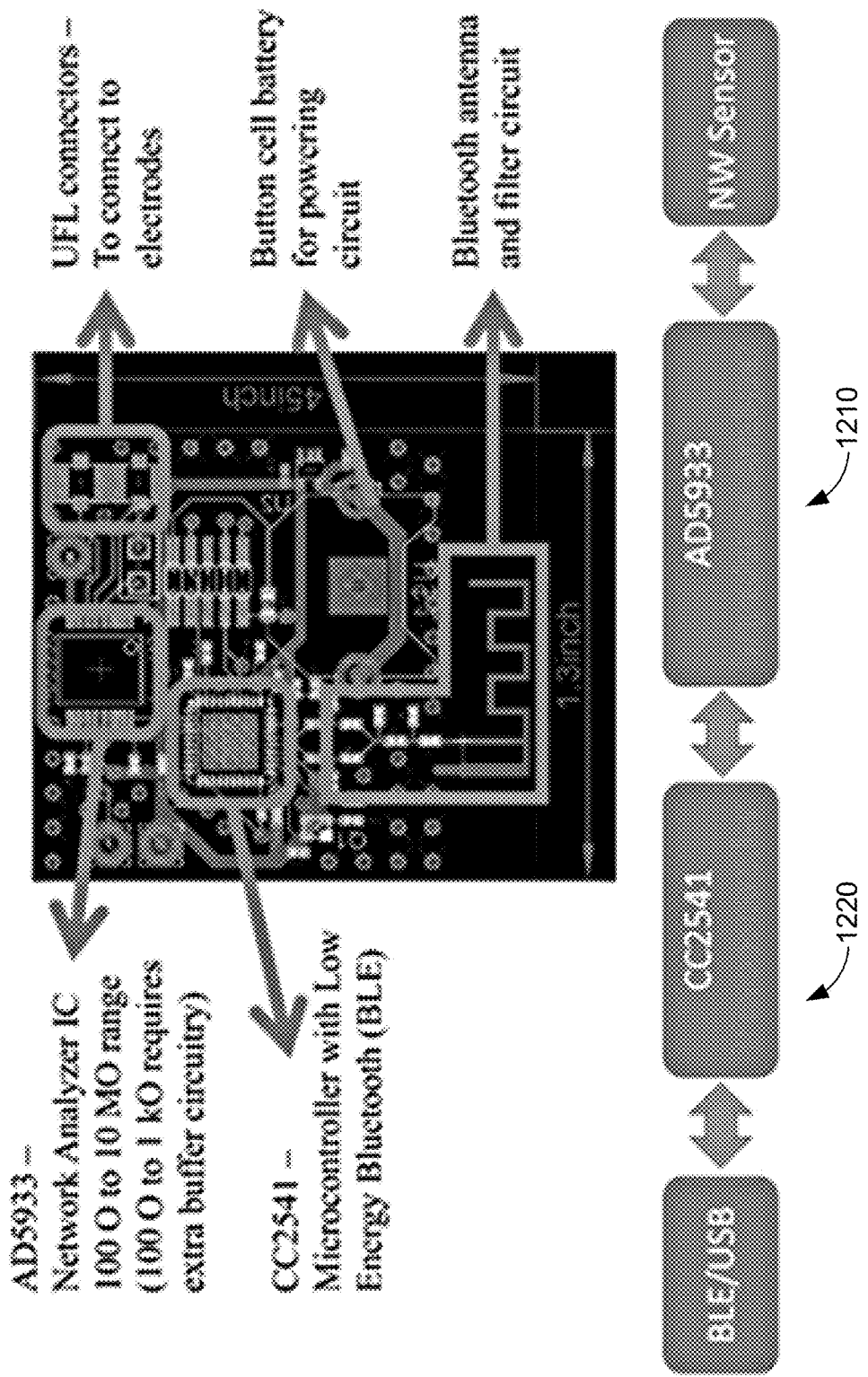
FIG. 10A illustrates a printed circuit board layout and block diagram of an example according to various embodiments.

To implement the hydration sensors described herein, a wristband was chosen as the first form factor due to the good user acceptance of wearing wristwatch like devices, although the sensor can also be integrated into an armband, a chest strap, or a headband. A small-scale, low power circuit was designed to acquire the signals and transmit the data wirelessly via Bluetooth® communication. In that context, an example printed circuit board (PCB) layout and block diagram of the personal hydration monitor is shown in FIG. 10A. The principle components were chosen to realize the desired functions at relatively low power, although other components could be used. In the example shown, the impedance was measured using an impedance network analyzer 1210, such as the AD5933 impedance network analyzer 1210 manufactured by Analog Devices®. In some embodiments, the impedance network analyzer 1210 can combine an on-board frequency generator with an analog-to-digital converter (ADC). The impedance network analyzer 1210 is coupled to an SOC processing and communications chip 1220, such as the CC2541 2.4-GHz Bluetooth® and SOC manufactured by Texas Instruments®. The CC2541 offers a power-optimized system on chip solution for low-power Bluetooth®, with an industry standard 8051 microcontroller, 256 kilobytes in-system programmable flash memory, and 8 KB random access memory.

Figure 10B:
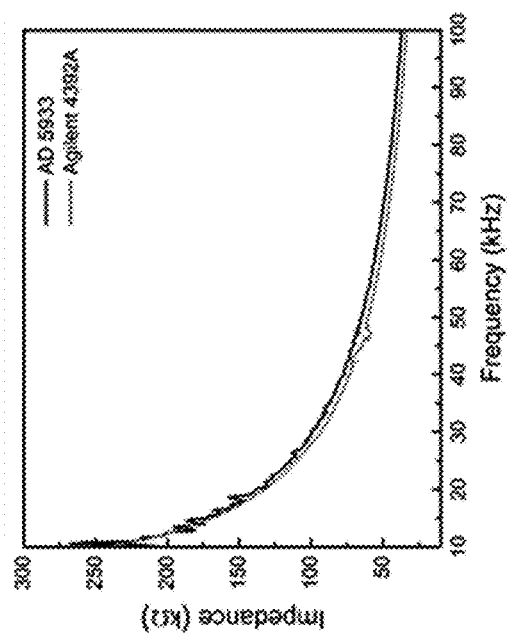
FIG. 10B illustrates a comparison of the impedance measurement from an electrode on artificial skin between a desktop impedance analyzer and a portable evaluation board according to various embodiments.

Impedance measurements on the same hydration sensor were performed using both the AD5933 network analyzer and a desktop impedance analyzer (i.e., HP Agilent® 4392A), sweeping the frequency from 10 to 100 kHz. The measured impedances using the AD5933 controlled by the CC2541 microcontroller and the impedance analyzer showed good agreement as shown in FIG. 10B. This indicates that the AD5933 impedance converter system is viable as a portable alternative to standard desktop impedance analyzers.

Figure 10E:
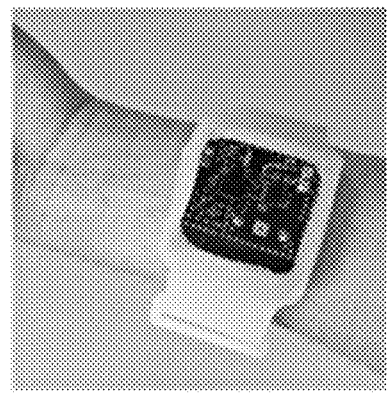
FIGS. 10C-10E illustrate an example rendering of an assembled portable hydration monitor, an exploded view of the portable hydration monitor, and a wrist band for the portable hydration monitor worn on a wrist like a watch, respectively.
Figure 10D:
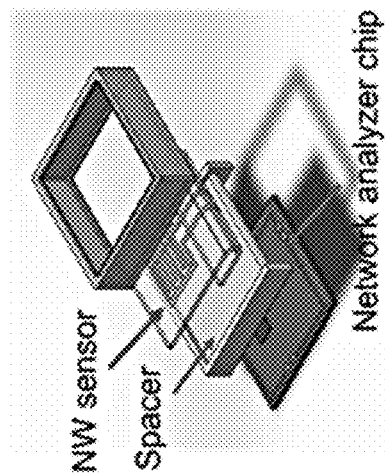
Figure 10C:
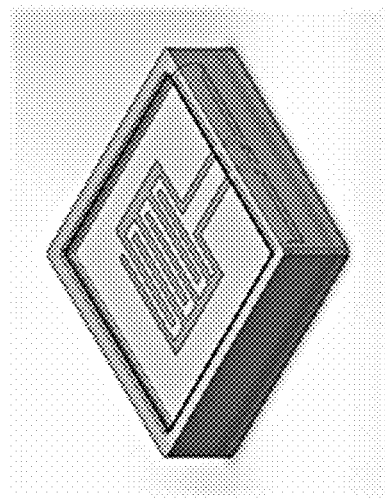

As shown in FIGS. 10C-10D, a PCB containing the impedance network analyzer 1210, the SOC processing and communications chip 1220, and a button cell battery was connected to the hydration sensor using micro coaxial cables and rubber epoxy that allows the connection to remain secure while still retaining the stretchable nature of the electrode. A 3D printed spacer was used to enable secure contact between the hydration sensor and the skin and isolate the sensing component from the electrical circuit. The PCB, spacer, and electrode were secured and worn on the body using a wristband as shown in FIG. 10E.

Figure 11:
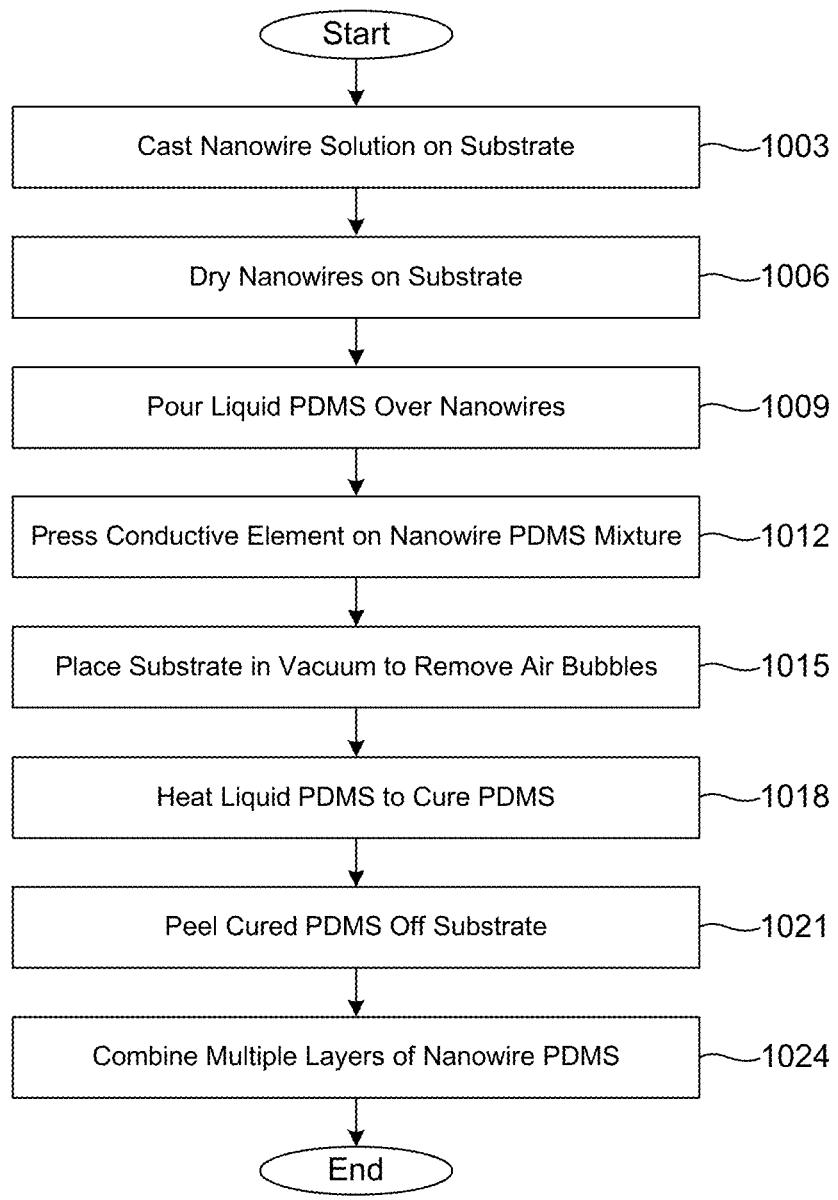
FIG. 11 illustrates an example flowchart of a process for fabricating the electrode shown in FIGS. 1-5 for a wearable hydration monitor according to various embodiments.

Referring next to FIG. 11, shown is a flowchart that provides one example of fabricating the electrode 103 shown in FIGS. 1-5 according to various embodiments. Starting with step 1003, a solution comprising nanowires, such as silver nanowires, are casted onto a substrate, for example, in a predefined arrangement. For example, a nanowire solution can be casted on the substrate such that parallel rows of nanowires will be created. To this end, a matrix of nanowires can be formed by combining multiple layers of nanowires. In alternative embodiments, a uniform layer of nanowires can be created, as illustrated in FIG. 7A. In various embodiments, the substrate can include silicon, plastic, glass, a combination thereof, or any other suitable substrate material.

Next, in step 1006, the nanowire solution on the substrate is dried such that liquid from the nanowire solution evaporates. As a result, a network of nanowires on the substrate remains in the predefined arrangement. Next, in step 1009, liquid PDMS is poured over the nanowires to create a mixture of nanowires and PDMS. As can be appreciated, the PDMS is poured to avoid changing or otherwise interfering with the arrangement of the nanowires. Next, in step 1012, one or more conductive elements, such as one or more lead wires, are pressed on top of the nanowire PDMS mixture before the nanowire PDMS mixture has dried or cured. In various embodiments, the one or more conductive elements can be configured to operatively connect to the measuring circuitry 409 and/or the processing circuitry 406.

Next, in step 1015, the substrate having the nanowire PDMS mixture can be placed in a vacuum to remove air bubbles from the mixture. In step 1018, the liquid nanowire PDMS mixture can be heated at a suitable temperature for a suitable amount of time to cure the PDMS. In various embodiments, the PDMS is cured in an oven at 100° C. for an hour; however, other temperatures and amounts of time can be implemented.

In step 1021, the cured PDMS is peeled off of the substrate, after which the network of nanowires is visibly bonded to the PDMS and the one or more lead wires are securely connected to the nanowire network. Finally, in step 1024, additional layers of nanowire PDMS can be combined, for example, to create a nanowire matrix or other arrangement of nanowires. However, in some applications, a single layer of nanowire PDMS can be suitable such that additional layers are not needed.

Figure 12:
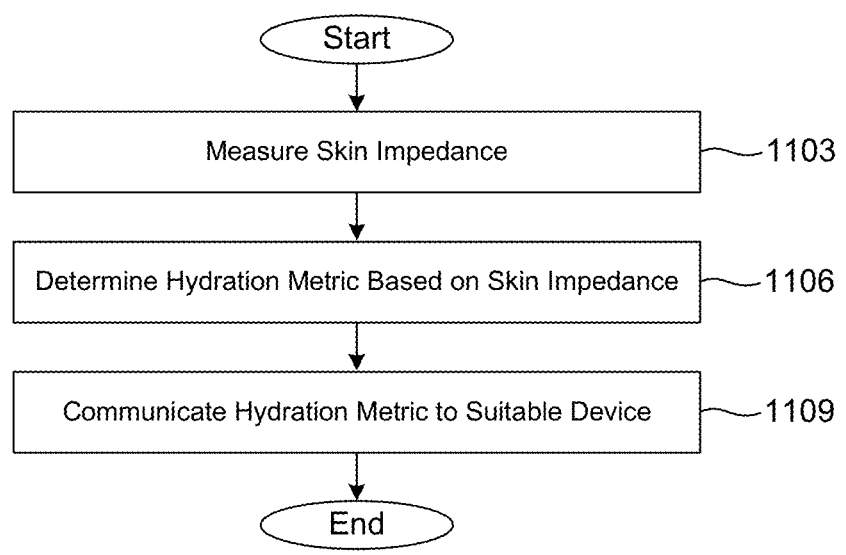
FIG. 12 illustrates an example flowchart of a process for the operation of a wearable hydration monitor according to various embodiments.

Referring next to FIG. 12, shown is a flowchart that provides one example of the operation of the monitoring device 100 according to various embodiments. It is understood that the flowchart of FIG. 14 provides merely an example of the many different types of functional arrangements that can be employed to implement the operation of the monitoring device 100 as described herein. As an alternative, the flowchart of FIG. 11 can be viewed as depicting an example of elements of a method implemented in the processing circuitry 406 according to one or more embodiments.

Beginning with step 1103, a skin impedance is measured using, for example, the measuring circuitry 409 and/or one or more electrodes 103 making direct or indirect contact with skin. The measuring circuitry 409 can include, for example, a network analyzer configured to measure skin impedance through the one or more electrodes 103. To this end, in some embodiments, the measuring circuitry 409 includes the AD5933 network analyzer.

Next, in step 1106, a hydration metric can be determined based on the skin impedance measured in step 1103. A hydration metric can be a percentage, an alphanumeric character, a symbol, or any other suitable identifier able to provide an indication of a hydration level of the person for which the skin impedance was measured. The hydration metric can be calculated by the processing circuitry 406 of the monitoring device 100 using a predefined formula. Alternatively, in various embodiments, the hydration metric can be calculated by another device.

Next, in step 1109, the hydration metric is communicated to a suitable device using, for example, the communication module 415 to render the hydration metric on a display 403. In various embodiments, the monitoring device 100 can communicate the hydration metric to a smartphone, smartwatch, laptop computing device, tablet computing device, or other suitable device capable of logging the hydration metric and/or presenting the hydration metric to a user.

The flowchart in FIGS. 11 and 12 show the functionality and operation of a monitoring device 100. If embodied in software, each block can represent a module, segment, or portion of code that includes program instructions to implement the specified logical function(s). The program instructions can be embodied in the form of source code that includes human-readable statements written in a programming language or machine code that includes numerical instructions recognizable by a suitable execution system such as a processor in a computer system or other system. The machine code can be converted from the source code, etc. If embodied in hardware, each block can represent a circuit or a number of interconnected circuits to implement the specified logical function(s).

Although the processes described herein identify a specific order, it is understood that the order can differ from that described. For example, the order of execution of two or more blocks can be scrambled relative to the order shown. Also, two or more blocks can be executed concurrently or with partial concurrence. Further, in some embodiments, one or more of the blocks can be skipped or omitted. In addition, any number of counters, state variables, warning semaphores, or messages might be added to the logical flow described herein, for purposes of enhanced utility, accounting, performance measurement, or providing troubleshooting aids, etc. It is understood that all such variations are within the scope of the present disclosure.

Disjunctive language such as the phrase "at least one of X, Y, or Z," unless specifically stated otherwise, is otherwise understood with the context as used in general to present that an item, term, etc., can be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

Therefore, the following is claimed:

1. A monitoring device, comprising:
   a flexible electrode configured to conform with a surface of skin, the flexible electrode comprising nanowires or nanoparticles embedded within a polydimethylsiloxane (PDMS) substrate and presenting a complex impedance when positioned in contact with skin;
   a housing configured to be positioned against the surface of skin with a band that secures the flexible electrode in position on the surface of skin, wherein the band comprises a wristband, an armband, a chest strap, or a headband; and
   processing circuitry positioned within the housing, the processing circuitry being communicatively coupled to the flexible electrode and configured to:
      present an excitation frequency to the complex impedance of the flexible electrode;
      sample a response of the complex impedance to the excitation frequency; and
      measure a level of hydration using the flexible electrode based on the response.

2. The monitoring device of claim 1, wherein the flexible electrode comprises silver nanowires or nanoparticles embedded within the PDMS substrate.

3. The monitoring device of claim 1, wherein the flexible electrode comprises at least two interdigitated silver nanowire electrodes that are electrically isolated from each other in a common layer of the PDMS substrate.

4. The monitoring device of claim 1, wherein the processing circuitry comprises impedance converter network analyzer circuitry.

5. The monitoring device of claim 4, further comprising a battery operable to power the processing circuitry.

6. The monitoring device of claim 1, wherein the processing circuitry is further configured to generate a hydration metric based on the level of hydration.

7. The monitoring device of claim 6, further comprising a display device configured to display the hydration metric.

8. The monitoring device of claim 6, further comprising a communication module configured to communicate the hydration metric to an external device.

9. The monitoring device of claim 1, wherein the flexible electrode is adapted for contact with skin.

10. The monitoring device of claim 1, within a smartwatch, a fitness band, or a patch.

11. A method, comprising:
    positioning a housing comprising a flexible electrode against a surface of skin, the flexible electrode positioned on a bottom side of the housing in contact with the skin;
    presenting, by processing circuitry, an excitation frequency to a complex impedance of the flexible electrode;
    sampling, by the processing circuitry, a response of the complex impedance to the excitation frequency; and
    measuring, by the processing circuitry, a level of hydration based on the response, wherein the flexible electrode is configured to conform with the surface of skin, comprises nanowires or nanoparticles embedded within a polydimethylsiloxane (PDMS) substrate, and presents the complex impedance when positioned in contact with skin.

12. The method of claim 11, wherein the flexible electrode comprises silver nanowires or nanoparticles embedded within the PDMS substrate.

13. The method of claim 11, wherein the excitation frequency is in the range of about 10-100 kHz.

14. The method of claim 11, further comprising displaying the level of hydration on a display device.

15. A monitoring device, comprising:
    a flexible electrode configured to conform with a surface of skin, the flexible electrode comprising at least two interdigitated silver nanowire or nanoparticle electrodes in a substrate comprising a polydimethylsiloxane (PDMS) substrate and presenting a complex impedance when positioned in contact with skin, the at least two interdigitated silver nanowire or nanoparticle electrodes being electrically isolated from each other in a common layer of the PDMS substrate; and
    processing circuitry configured to measure a level of hydration using the flexible electrode.

16. The monitoring device of claim 15, wherein the processing circuitry is configured to:
    present an excitation frequency to the complex impedance of the flexible electrode;
    sample a response of the complex impedance to the excitation frequency; and
    measure the level of hydration based on the response.

17. The monitoring device of claim 15, wherein the processing circuitry comprises impedance converter network analyzer circuitry.

18. The monitoring device of claim 15, further comprising a battery operable to power the processing circuitry.

19. The monitoring device of claim 15, wherein the processing circuitry is further configured to generate a hydration metric based on the level of hydration.

20. The monitoring device of claim 19, further comprising a display device configured to display the hydration metric.

* * * * *